United States Patent [19]

Matthes et al.

[11] Patent Number: 4,963,662
[45] Date of Patent: Oct. 16, 1990

[54] FLUORINATED NUCLEOSIDES AND METHOD FOR TREATING RETROVIRUS INFECTIONS THEREWITH

[75] Inventors: Eckart Matthes; Christine Lehmann; Dieter Scholz; Martin von Janta-Lipinski; Klaus Gaertner; Peter Langen; Hans-Alfred Rosenthal, all of Berlin, German Democratic Rep.

[73] Assignee: Akademie der Wissenschaften der DDR, Berlin, German Democratic Rep.

[21] Appl. No.: 223,677

[22] Filed: Jul. 15, 1988

Related U.S. Application Data

[63] Continuation-in-part of Ser. No. 65,952, Jun. 24, 1987, abandoned.

[30] Foreign Application Priority Data

Jul. 24, 1986 [DD] German Democratic Rep. ..................... 2928263
May 8, 1987 [DD] German Democratic Rep. ..................... 3025732
Jun. 3, 1987 [DD] German Democratic Rep. ..................... 3034896

[51] Int. Cl.$^5$ ..................... C07H 19/06; A61K 31/70
[52] U.S. Cl. ......................... 536/23; 536/24; 536/26; 536/27; 536/29
[58] Field of Search ................. 536/23, 24, 26, 27–29; 514/45–51

[56] References Cited

U.S. PATENT DOCUMENTS 3,775,397 11/1973 Etzold et al. ................. 536/23

FOREIGN PATENT DOCUMENTS 158903 2/1983 Fed. Rep. of Germany .
2240622 10/1987 Japan .

Primary Examiner—John W. Rollins
Attorney, Agent, or Firm—Schweitzer Cornman & Gross

[57] ABSTRACT

A method for treating AIDS, which comprises administering to a patient in need therefor a pharmaceutical composition comprising a therapeutically effective amount of a compound having the formula

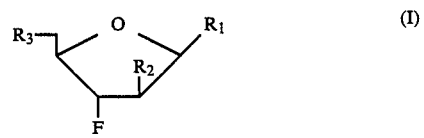

wherein
$R_1$ is an adenine, cytosine, guanine, thymidine, uracil, 5-substituted uracil, 5-substituted cytosine derivative, 2-fluoroadenine, 2.6-diaminopurine, 2-aminopurine, 6-thioguanine, or 7-deazaadenine group;
$R_2$ is H, or a OH group;
$R_3$ is a OH, O-acyl, O-palmitoyl group, or phosphates (as free acid, or its alkali, ammonium or alkyl ammonium salts), or any other precursor group for the hydroxyl group;

or a physiologically acceptable salt thereof. Furthermore, the present invention comprises the new compounds:
2',3'-dideoxy-3'-fluoro-2-fluoroadenosine,
2',3'-dideoxy-3'-fluoro-6-thioguanosine,
2',3'-dideoxy-3'-fluoro-2,6-diaminopurineriboside,
2',3'-dideoxy-3'-fluoro-2-aminopurineriboside,
2',3'-dideoxy-3'-fluoro-5-aminomethyluridine,
2',3'-dideoxy-3'-fluoro-5-azidomethyluridine, and
2',3'-dideoxy-3'-fluoro-5-hydroxymethyluridine.

8 Claims, No Drawings

FLUORINATED NUCLEOSIDES AND METHOD FOR TREATING RETROVIRUS INFECTIONS THEREWITH

This is a continuation-in-part application for U.S. patent application Ser. No. 65,952, filed on June 24, 1987, now abandoned.

FIELD OF THE INVENTION

The invention relates to fluorinated nucleosides and process for treating retrovirus infections, particularly of HIV type 1 and HIV 2 infections.

BACKGROUND OF THE INVENTION

Acquired immune deficiency syndrome (AIDS) has been known for only a few years as a new infectious disease in man. It is caused by the recently discovered retroviruses HIV 1 and HIV 2, which infect and destroy preferentially CD4+ T-helper lymphocytes. An immune deficiency is thus produced. This is manifested by the occurrence of opportunistic infections of Kaposi's sarcoma and of so called AIDS-encephalopathy, which are generally progressive and inevitably lead to death. The development of AIDS and the preceding lymphadenopathy syndrome are dependent on active virus replication, which is closely related to the activity of the viral enzyme reverse transcriptase. Therefore effective and selective inhibitors of this polymerase raise the possibility of preventing and slowing the progress of AIDS. The first clinically tested inhibitors of HIV reverse transcriptase, such as Suramin (Germanin TM) and HPA 23, have not reached the required level of tolerability of the human body. Only 3'-azido-2,3'-deoxy-thymidine ($N_3$-TdR) (German Federal Republic Pat. No. 3,608,606) has shown an unequivocal life extending effect in the case of AIDS patients with pneumocystis carinii pneumoniae, accompanied by improvements in clinical and neurological findings and a temporary restoration of certain immunological functions (Mitsuya et al., Nature 325, 773, 1987). However, the toxic side effects on the bone marrow required blood transfusions in about 50% of the patients treated with it. This indicates that inhibitors of HIV reverse transcriptase with higher selectively and efficacy are required.

DESCRIPTION OF THE INVENTION

It was found that a mono- or polysubstituted pyrimidine- or purine nucleoside having the formula

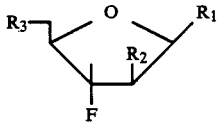

(I)

wherein:

$R_1$ is an adenine, cytosine, guanine, thymine, uracil, 5-substituted uracil, 5-substituted cytosine derivative, 2-fluoroadenine, 2,6-diaminopurine, 2-aminopurine, 6-thioguanine, or 7-deazaadenine group;

$R_2$ is H, or a OH group;

$R_3$ is a OH, O-acyl, O-palmitoyl group, or phosphates (as free acid, or its alkali, ammonium or alkyl ammonium salts), or any other precursor group for the hydroxyl group;

or a physiologically acceptable salt thereof, by itself or with a physiologically acceptable carrier, is effective retrovirus infections, particularly infections with HIV types 1 and 2.

The invention comprises a process for treating AIDS, by administering to a patient in need therefore a pharmaceutical preparation containing as active ingredient a therapeutically effective amount of at least one compound of formula (I). The invention also comprises the following new compounds.

2',3'-dideoxy-3'-fluoro-2-fluoroadenosine,
2',3'-dideoxy-3'-fluoro-6-fluoroadenosien,
2',3'-dideoxy-3'-fluoro-2,6-diaminopurineriboside,
2',3'-dideoxy-3'-fluoro-2-aminopurine riboside,
2',3'-dideoxy-3'-fluoro-5-aminomethyluridine,
2',3'-dideoxy-3'-fluoro-5-azidomethyluridine, and
2',3'-dideoxy-3'-fluoro-5-hydroxymethyluridine.

Various compounds are referred herein by abbreviated names. The following tabulation provides an explanation of those abbreviations.

| abbreviation | complete name of compound |
|---|---|
| dTMP | 2',3'-dideoxythymidine-5'-monophosphate |
| FTdR | 2',3'-dideoxy-3'-fluorothymidine |
| FtMP | 2',2'-dideoxy-3'-fluorothymidine-5'-monophosphate |
| FdTTP | 2'-3'-dideoxy-3'-fluorothymidine-5'-triphosphate |
| FddUrd | 2'-3'-dideoxy-3'-fluorouridine |
| FdUTP | 2'-3'-dideoxy-3'-fluorouridine-5'-triphosphate |
| FddFUrd | 2'-3'-dideoxy-3'-fluoro-5'-fluorouridine |
| F5FdUTP | 2'-3'-dideoxy-3'-fluoro-5-fluorouridine-5'-triphosphate |
| FddBrUrd | 2'-3'-dideoxy-3'-fluoro-5-bromouridine |
| FddCNUrd | 2'-3'-dideoxy-3'-fluoro-5-cyanouridine |
| FddHMUrd | 2'-3'-dideoxy-3'-fluoro-5-hydroxymethyluridine |
| FddEtUrd | 2'-3'-dideoxy-3'-fluoro-5-ethyluridine |
| F5EtdUTP | 2'-3'-dideoxy-3'-fluoro-5-ethyluridine-5' triphphosphate |
| FddCyt | 2'-3'-dideoxy-3'-fluorocytidine |
| FddMCyt | 2'-3'-dideoxy-3'-fluoromethylcytidine |
| FddGuo | 2'-3'-dideoxy-3'-fluoroguanosine |
| FdGTP | 2'-3'-dideoxy-3'-fluoroguanosine-5'-triphosphate |
| FddAdo | 2'-3'-dideoxy-3'-fluoroadenosine |
| FddDAPR | 2'-3'-dideoxy-3'-fluoro-2,6-diaminopurineriboside |
| FaraU | 3'-deoxy-3'-fluoroarabinosyluracil |
| FaraBrU | 3'-deoxy-3'-fluoroarabinosyl-5-bromouracil |
| FaraC | 3'-deoxy-3'-fluoroarabinosylcytosine |
| $N_3$-TdR | 3'-azido-2',3'-dideoxythymidine. |

The pyranose and the furanose forms are in equilibrium with each other. Accordingly, the furanose nomenclature was chosen for naming the arabinose compounds.

A. Inhibition of HIV associated reverse transcriptase

At first the triphosphates of some compounds according to formula I were investigated for their ability to inhibit the polymerization of artificial templates (such as polyA.oligodT and polyC.oligodG) catalyzed by HIV-associated reverse transcriptase (HIV-RT)according to the method described by A. D. Hoffman et al., Virology 147, 326, 1985. Table 1 demonstrates the concentrations required for a 50% inhibition of this viral enzyme ($ID_{50}$). $FdTTP_1$, FdUTP and FdGTP are among the strongest inhibitors found so far for HIV-RT. In comparison the $ID_{50}$ for 3'-azidothymidinetriphosphate was estimated under our conditions to be about 0.05 $\mu$M. Examination of the mode of action revealed, at least for FdTTP, a competitive type of inhibition rather than a DNA chain terminating incorporation.

In contrast to FdTTP, the corresponding 3'-chloro-2',3'-dideoxythymidine triphosphate was shown to be completely ineffective against HIV-associated reverse transcriptase at 1 μM, indicating that for a high degree of efficiency the nature of the 3'-substituent plays a critical role and cannot be simply replaced by any other group.

TABLE 1

Comparison of concentrations of 2',3'-dideoxy-3'-fluoronucleoside 5'-triphosphates required for a 50% inhibition ($ID_{50}$) of HIV-reverse transcriptase (HIV-RT) and the cellular DNA polymerases α

| | Compound | HIV-RT | $ID_{50};\mu M$ cellular polymerases | |
|---|---|---|---|---|
| | | | α | β |
| A | FdTTP | 0.05 | >200 | 2.2 |
| B | FdUTP | 0.07 | >200 | 3.0 |
| C | FdGTP | 0.05 | >200 | 1.8 |
| D | F5FdUTP | 0.45 | >200 | 15.0 |
| E | F5EtdUTP | 7.5 | 10 | 4.0 |

B. Effect on cellular DNA polymerases α and β

The strong inhibiting effect of 3'-fluoro-substituted deoxynucleotides against HIV-reverse transcriptase can be utilized therapeutically only if the cellular DNA polymerases, especially the DNA polymerase α which is required for the replication of the cellular DNA, remain substantially unaffected. As shown in Table 1, this could be confirmed for DNA polymerase α. A 50% inhibition of this cellular DNA polymerase has not been reached at 200 μM of the tested compounds demonstrating their high selectivity. The $ID_{50}$ values for the DNA polymerase β responsible for cellular DNA repair vary between 1.8-15 μM. Both enzymes were purified from calf thymus and tested according to the method of E. Matthes et al., Biomed. Biochem. Acta 44, K63 (1985).

C. The intracellular phosphorylation of FTdR

The critical factor for 3'-fluoro deoxynucleosides to reach a high intracellular efficiency is their ability to be phosphorylated in situ in the infected cells. A lack of phosphorylation of 3'-modified deoxynucleosides may strongly reduce or even abolish the efficiency of a compound which proved to be highly effective in the HIV reverse transcriptase test, as in the case of 2',3'-dideoxythymidien. As shown in Table 2, FTdR is metabolized sufficiently to the triphosphate in all examined cell lines during a 24-hour incubation. The concentrations of FdTTP determined for uninfected human H9- and CEM-cells are in the same range as found for HTLV-$III_B$ (HIV-1) infected H9-cells and LAV-II (HIV-2) infected B CEM-cells, respectively, so that an AIDS virus infection of T-cells apparently does not change the ability of FTdR to be phosphorylated. By comparison, the phosphorylation of 50 μM $N_3$-TdR by HTLV-$III_B$-infected H9 cells to triphosphate during a 24-hour incubation has been reported to reach only 0.9 pmoles/$10^6$ cells and to be accompanied by an extreme accumulation of the monophosphate of $N_3$-TdR (460 pmoles/106 cells), reflecting a strong inhibition of the dTMP-kinase (Furman et al, Proc. Natl. Acad. Sci. USA 83 8333 (1986)) and entailing considerable alterations of the deoxynucleoside triphosphate substrate pools (Furman et al., loc cit.) which affect cellular DNA synthesis. FTdR does not have this adverse effect on the thymidylate kinase (see Table 2), so that the significant changes of the cellular pools of deoxynucleoside-triphosphates are not to be expected, although FTdR is distinctly better phosphorylated than $N_3$TdR.

TABLE 2

Synthesis of nucleotides from 1μ$M^3$ H-FTdR (tritium labeled) in cells of various species within 24 hours.

| | | pmoles/$10^6$ cells phosphate | | |
|---|---|---|---|---|
| | Cell line | mono- (FdTMP) | di- (FdTDP) | tri- (FdTTP) |
| Human | MT4 | 9.0 | 1.6 | 5.6 |
| | CEM (LAV-II) | 6.1 | 0.5 | 2.8 |
| | H9 (HTLV-$III_2$) | 3.3 | 0.3 | 1.4 |
| Rat | NRK-49F | 3.5 | 3,7 | 13.2 |
| Mouse | 3T3 | 0.38 | 2.2 | 16.3 |

D. Resistance of 3'-fluoro-substituted pyrimidine-nucleoside analogs against phosphorolytic cleavage Some thymidine antimetabolites, such as 5-iodideoxyuridine, 5-bromodeoxyuridine and 5-bromovinyldeoxyuridine will be cleaved to a large extent by human thymidine-phosphorylase to inactive pyrimidine bases and sugar phosphates. This proved to be a most limiting factor with respect to their systemic in vivo applicability. Therefore FTdR, FddBrUrd and FddFUrd were investigated for their ability to be cleaved by thymidine-phosphorylase from human spleen. We have found that these compounds at 1 mM were cleaved within 3 hours only to an extent of 3-8% and can be considered as being resistant to this enzyme in comparison to thymidine (90% cleavage in 2 hours).

E. Inhibition of the cytopathic effect of HIV on MT-4 cells by 3'-fluoro-substituted deoxynucleosides Under in vitro conditions immortalized T-lymphocytes can be killed within few days by the cytopathic effect of HIV. We determined the actual efficacy of 3'-fluro-substituted deoxynucleosides in protecting a T-cell-line against the cytopathic effect of HIV. For this purpose about 20,000 MT-4 cells (Harada et al. Science 229, 563 (1985)) were infected with HIV (titer: 0.04 mol) and incubated in the presence of varying concentrations of compounds according to formula I, with 10% fetal calf serum (FCS) in 200 μl RPMI medium. After 6 days of incubation the viable cells were counted that were excluded from trypan blue staining.

Table 3 summarizes the results given as concentrations required for a 50% protection of the cells against the cytopathic effect of HIV ($ED_{50}$) and as a concentrations producing a 50% inhibition of cell proliferation ($CD_{50}$). The following compounds proved to be most effective and selective: FTdR, FddUrd, FddBrUrd, FddDAPR and FddGuo. For FTdR and $ED_{50}$ was 0.003 μM and in a direct comparison for $N_3$-TdR this value was estimated to be 0.016 μM, indicating a 5 times higher antiviral activity of FTdR against $N_3$-TdR.

TABLE 3

Comparative potency and selectivity of 2',3'-dideoxy-3' fluoronucleosides as inhibitors of HIV-replication in MT-4 cells

| Compound | 50% antiviral dose ($ED_{50}$); μM | 50% cytotoxic dose ($CD_{50}$); μM |
|---|---|---|
| FTdR | 0.003 | 1.1 |
| FddUrd | 0.275 | 75 |
| FddFUrd | not detectable | >200 |
| FddBrUrd | 5 | 190 |
| FddCNUrd | not detectable | >500 |
| FddHMUrd | >500 | >500 |
| FddEtUrd | >500 | >500 |
| FddCyt | 25 | 62 |
| FddMCyt | 125 | 1.25 |
| FddGuo | 5 | 250 |
| FddAdo | >100 | 75 |
| FddDAPR | 6 | 480 |
| FaraU | >500 | >500 |

TABLE 3-continued

Comparative potency and selectivity of 2',3'-dideoxy-3' fluoronucleosides as inhibitors of HIV-replication in MT-4 cells

| Compound | 50% antiviral dose (ED$_{50}$); μM | 50% cytotoxic dose (CD$_{50}$); μM |
|---|---|---|
| FaraBrU | >100 | >100 |
| FaraC | >100 | >100 |

The combined inhibitory effect of a 3'-fluoro-substituted pyrimidine nucleoside (FTdR, FddUrd) and a 3'-fluoro-substituted purine nucleoside (FddGuO, FddDAPR) on HIV induced cytopathic effect on MT-4 cells was examined and analyzed by the isobologram method [M. Baba et al. Antimicrob. Agents Chemother. 25. 515 (1985)]. The calculated fractional inhibitory concentrations (FIC) of the compounds combined (e.g. FIC$_{FTdR}$+FIC$_{FddGuo}$; FIC$_{FddUrd}$+FIC$_{FddDAPR}$) provided a minimum FIC index between 0.5 to 1.0 indicating an additive to subsynergistic effect for these combinations, which do not reduce the viability of the MT-4 cells.

The foregoing data unequivocally establish in vitro the AIDS virus-inhibiting effect of the compounds of formula (I). However, in view of the current limitations on testing possibilities no in vivo dosage ranging could be carried out as yet. The term "therapeutically effective dose" as used in the specification and claims, means a dose of a pharmaceutical preparation containing an active ingredient a compound of formula (I), in an amount effective to bring a therapeutic benefit, but without an undue toxic effect. The therapeutically effective dosage level can be established in each given case by routine experimentation. Some guidelines are provided by the data in Table 3 and by the following experiments.

F. Cytotoxicity of FTdR and FddUrd in human cell cultures

Originally FTdR was developed as a cytostatic agent (P. Langen et al., Acta biol. med. Germ. 23, 759, 1969; and U.S. Pat. No. 3,775,397) and, therefore, its cytostatic efficacy has been examined in extensive prior studies. The examinations and tests conducted by the NCI program in the USA against 9 different animal tumors concluded that FTdR has only a weak cytostatic effect. Ehrlich-mouse-ascites-carcinoma cells (EMAC) represents an exception to that finding, and this is probably based on its high capability to phosphorylate FTdR, which is 10 times higher than in human cells. The fast reversibility of the cytostatic effects on EMAC cells was regarded as a special property of this compound (P. Langen et al., Europ. J. Cancer. 14, 349, 1978). The antiproliferative effect of FTdR and FddUrd, and in comparison thereto of N$_3$-TdR were tested on human cell lines with regard to a possible use in humans. Table 4 shows on the basis of the available CD$_{50}$ values that the cytostatic effects of FTdR and N$_3$-TdR vary considerably between different cell lines. When FTdR is compared to N$_3$-TdR, the effect are very similar, however somewhat lower in each case for N$_3$-TdR. In contrast, FddUrd does not show any substantial antiproliferative effect.

TABLE 4

Inhibition of proliferation of human cell-lines by FTdR and FddUrd in comparison to N$_3$-TdR CD$_{50}$; μM

| Cells | Deviation | N$_3$-TdR | FTdR | FddUrd |
|---|---|---|---|---|
| K-562 | acute myeloic leukemia | 50 | 45 | >1,000 |
| REH | acute lymphatic leukemia | 220 | 160 | 9,000 |
| K-37 | immortalized T-cells | 500 | 260 | >1,000 |
| H9 | immortalized T-cells | 800 | 1000 | >2,500 |

CD$_{50}$: inhibitory dose required to reduce the cell number by 50%

G. Effects of FTdR on mice infected with Rauscher murine leukemia virus (RLV)

At the present time there is no appropriate animal model available for testing anit AIDS-drugs. Therefore we examined the toxicity and antiretroviral activity of FTdR in mice infected with Rauscher murine leukemia virus. Different doses of FTdR were applied to BalB/c Hans strain of mice in drinking water for 20 days beginning 2-8 hours after RLV infection. Such a continuous application of FTdR at 69.0 mg/kg/day was able to prevent the development of a leukemia induced normally by this retrovirus within 3 weeks. As shown in Table 5 line F this concentration completely suppresses the appearance of splenomegaly as well as of RLV-associated reverse transcriptase activity in the serum. However toxic side effects are associated with this concentration range as demonstrated by hematological parameters (Table 5, E and F). FTdR applied to a 10-fold lower concentration (6.5 mg/kg/day) failed to produce signs of anemia and depression of white cell counts but, nevertheless, it seems to be completely active in suppressing splenomegaly and viremia, as estimated by reverse transcriptase activity, see Table 5, lines C and D. A further reduction of the oral FTdR dose to 1.8 mg/kg/day, given for 24 days caused still more than 25% decrease of serum reverse transcriptase activity and more than 50% suppression of splenomegaly. These data show clearly that FTdR is able to protect mice even 2-3 hours after an infection with a retrovirus (RLV). A direct investigation of the inhibitory activity of the triphosphate of FTdR (FdTTP) on the RLV-associated reverse transcriptase has shown that the concentrations required for a 50% inhibition of this enzyme (ID$_{50}$) is 0.5 μM, i.e., this enzyme is 10 times less sensitive to the inhibitor than the HIV-associated reverse transcriptase (ID$_{50}$=0.05 μM). These results, in addition to the very effective phosphorylation of FTdR by human cells, let us assume that doses of FTdR could be sufficient for the treatment of AIDS, that are several times lower than required for a complete suppression for RLV infection in mice (6.5 mg/kg/d).

TABLE 5

Effects of continuous application of 6.5 or 69.0 mb/kg/day FTdR administered in the drinking water for 20 days on toxicity and development of RLV induced leukemia

| | | RLV | No. of mice | changes of body weight (%) | Hemoglobin (mMoles/l) | White blood cell count (per mL) | mean spleen weight (mg) | Reverse transcriptase (RT) serum (%)* |
|---|---|---|---|---|---|---|---|---|
| Control | A | − | 7 | ++5 | 10.6 | 5740 | 101 | — |
| | B | + | 10 | +10 | 7.2 | 4970 | 983 | 100 |
| FTdr | C | − | 5 | +1 | 8.9 | 5240 | 125 | — |
| 6.5 mg/kg/day | D | + | 10 | 0 | 8.1 | 4510 | 193 | 0 |
| FTdR | E | − | 5 | −12 | 4.3 | 1027 | 72 | — |

TABLE 5-continued

Effects of continuous application of 6.5 or 69.0 mb/kg/day FTdR administered in the drinking water for 20 days on toxicity and development of RLV induced leukemia

|  | RLV | No. of mice | changes of body weight (%) | Hemoglobin (mMoles/l) | White blood cell count (per mL) | mean spleen weight (mg) | Reverse transcriptase (RT) serum (%)* |
|---|---|---|---|---|---|---|---|
| 69.0 mg/kg/day F | + | 10 | −10 | 5.1 | 733 | 86 | 0 |

The advantages of FTdR are summarized below:

5-fold the efficacy in comparison to $N_3$-TdR in a cellular test;

better phosphorylation than $N_3$-TdR in human cell lines;

resistance against TdR-hosphorylase;

lower effects than $N_3$-TdR on TMP-kinase and also the dNTP-substrate pools;

tolerable and, especially reversible cellular toxicity.

Other effective compounds for use in accordance with the present invention, include:

2',3'-dideoxy-3'-2-fluoroadenosien;
2',3'-dideoxy-3'-6-thioguanosine;
2',3'-dideoxy-3'-2-aminopurineriboside;
3'-deoxy-3'-fluoroarabinosyladenine;
3'-deoxy-3'-fluoroarabinosylthymine;
2',3'-dideoxy-3'-fluoro-5-fluorocytidine;
2',3'-dideoxy-3'-fluoro-5-formylcytidine;
2',3'-dideoxy-3'-fluoro-5-aminouridine;
2',3'-dideoxy-3'-fluoro-5-azidouridine; and
2',3'-dideoxy-3'-fluoro-5-chlorouridine.

The invention also includes a method for the treatment or prophylaxis of AIDS in a human patient, which comprises administration of an agent containing a therapeutically effective amount of one or more of the compounds of formula (I) or a physiologically acceptable salt thereof to the patient, to produce an ameliorating effect on the HIV disease. The agent to be administered in accordance with the present invention contains one or more active substances of formula (I), together with one or more physiologically acceptable carriers, together with optional other therapeutically active ingredients. The agents are produced as a unit dose or multiples thereof. Each carrier that is used must be tolerable by the human patients, compatible with the other ingredients, and should not be harmful to patients.

The drugs of the present invention include all of those dosage forms which can be administered orally, rectally, nasally, topically, vaginally, or parenterally (including subcutaneously, intramuscularly, intravenously and intradermally). One or more active ingredients in accordance with formula (I) are contacted with the carrier which itself may also comprise one or more components and, if required, are then brought to a required galenic shape or form.

Drugs in accordance with the present invention for oral administration can be in the form of, tables, capsules, powder, or granules which contain a predetermined amount of the active ingredient of formula (I). A solution or suspension can also be employed. Optionally, taste masking agents or the like can be added.

Drugs for rectal administration can be in the form of suppositories in a suitable base.

Drugs for vaginal administration can be in the form of suppositories, pessaries, tampons, creams, gels, pastes, foams, or spray products.

Parenteral administration can be accomplished in a unit dose of the active ingredient of formula (I), or in a multiple dose thereof, and can be stored, e.g., in ampoules, vials, or in freeze dried condition. Freshly prepared injectable solutions and suspensions can be also made from sterile powders, granulates and tablets. This can be achieved, for example, by dissolving the active ingredient of formula (I) in physiological salt solution, in glucose or in order media that are suitable for intravenous injection or infusion. For the treatment of AIDS patients suitably a 3% solution is prepared of the required amount of e.g. FTdR in a physiological salt solution. This is sterilized and within an hour of preparation is administered to the patient by intravenous infusion. The infusion is repeated every 4–8 hours and is continued for at least 8–10 days.

The 3'-fluorinated nucleosides can be converted to a physiologically acceptable phosphate, or another ester by reaction with a phosphorylating agent, such as $POCl_3$, or a suitable esterifying agent, such as an acidhalogenide, or -anhydride [M. Yoshikawa et al., Tetrahedron Letters, 5065–68 (1967); D. E. Hoard et al., J. Am. Chem. Soc. 87, 1785–1788 (1965)]. The compounds of formula (I) containing phosphate groups can be converted, in a manner known per se, into their physiologically acceptable salts, such as by treatment with a suitable base.

Preferred esters of the compounds in accordance with formula (I) include carbonic acid esters in which the non-carboxy part of the ester group comprises a straight-chain, or branched-chain alkyl, alkoxyalkyl (e.g. methoxymethyl), aralkyl (e.g. benzyl), aryl (e.g. unsubstituted phenyl, or substituted with halogen, $C_{1-4}$ alkyl, or $C_{1-4}$ alkoxy), mono-, di-, and triphosphate esters, and sulfonate esters, such as alkyl- or aralkylsulfonyloxy (e.g. methanesulfonyloxy, or p-toluenesulfonyloxy.

The following examples provide a further illustration of the present invention the full scope of which is defined by the claims. Any reference to a "compound of the invention" is meant to refer to a compound defined by formula (I).

EXAMPLE 1

Injection solution

The required amount of a 3% solution is prepared from FTdR and physiological salt solution.

EXAMPLE 2

Uncoated or coated tablets

Powdered FTdR is formed into uncoated and coated tablets with one or more of the customary carriers, such as starch, talcum, magnesium stearate, potassium stearate, stearic acid, solid paraffin, cetyl alcohol, pectin, saccharose, arab gum, dextrin.

EXAMPLE 3

Preparation of 5-substituted 2',3'-dideoxy-3'-fluorouridines by cleavage of the 2',3'-anhydro bond (a) 1-(2',3'-Dideoxy-3-fluoro-β-D-ribofuranosyl)-5-ethyluracil A mixture of 2.30 g (mMol) 2,3'-anhydro-1-(2-deoxy-5-O-acetyl-β-D-xylofuranosyl)-5-ethyluracil, 2.5 g aluminum trifluoride and 300 ml 1.4 dioxane, containing 0.5% hydrogen fluoride, was heated in a steel vessel to 110° C. for 1.5 hours. After cooling, 100 ml water and 20 g $CaCO_3$ were added to the reaction solution. The filtered solution was concentrated to a syrupy consistency, which was dissolved in 50 ml methanol saturated with ammonia at 0° C. and stored for 24 hours at room temperature. After expelling the solvent under vacuum the obtained oil was subjected to column chromatography on silica gel eluted with chloroform/methanol (9/1 vol/vol. The title compound was obtained after solvent evaporation from the corresponding fractions as a solid substance MP: 183°–184° C.; MS, m/z 258 (M+).

(b) 5-Bromo-1-(2,3-dideoxy-3-fluoro-β-D-ribofuranosyl)uracil

A mixture of 5.31 g (10 mMol) 2,3'-anhydro-5-bromo-1-(2-deoxy-5-O-trityl-β-D-ribofuranosyl) uracil, 5.5 g aluminium trifluoride, and 400 ml 1.4-dioxane containing 0.5% hydrogen fluoride, was heated in a steel container to 110° C. for 1 hour. After cooling, the reaction solution was worked up as demonstrated in Example 3(a) to give a pale yellow crystalline material, MS: m/z 309 (M+, $C_9H_{10}N_2O_4BrF$).

EXAMPLE 4

Preparation of 5-substituted 2',3'-dideoxy-3'-fluorouridines by radical bromination of the 5-methyl group in FTdR and subsequent nucleophilic substitution of the bromine.

(a) 5-(Bromomethyl)-1-(5-O-acetyl-3-deoxy-3-fluoro-β-D-ribofuranosyl) uracil

5'-O-acetyl-3'-fluorothymidine (2.88 g 10 mMol) was heated in 250 ml 1.2-dichloroethane to complete dissolution under reflux. Thereafter 12 mMol elementary bromine was introduced into the solution by a stream of nitrogen and the solution irradiated with a photolamp (500 W lamp made by NARVA). The reaction was terminated after 2–3 hours. The solvent was removed under vacuum under formation of a viscous oil. The latter contained the title compound in a purity sufficient for the subsequent reactions.

(b) 1-(2,3-Dideoxy-3-fluoro-β-D-ribofuranosyl)-5-hydroxymethyluracil

The bromination product obtained from 2.86 g (10 mMoles) 5'-O-acetyl-3'-fluorothymidine in step (a) was dissolved in 50 ml 1.4-dioxane, mixed with 30 ml saturated sodium bicarbonate solution, and stirred for 1 hour at room temperature. Subsequently, the reaction solution was extracted with 5×30 ml chloroform. The united chloroform extracts were dried over sodium sulfate filtered and concentrated under vacuum to give a syrupy oil. After the customary treatment in 50 ml methanol/ammonia (saturated at 0° C.) this product yielded the title compound, which was obtained in crystalline form from ethanol. M.P. 184° C.; MS: m/z 260 (M+, $C_{10}H_{13}O_5N_2F$).

(c) 5-Aminomethyl-1-(2,3-dideoxy-3-fluoro-β-D-ribofuranosyl)uracil

The brominated product obtained from 2.86 g (10 mMoles) 5'-O-acetyl-3'-fluorothymidine in step (a) was dissolved in 50 ml 1,4-dioxane. This reaction solution was cooled at 0° C. and gaseous ammonia was bubbled through it. After 40 minutes of stirring in the ammonia atmosphere, the mixture was filtered to remove salts, and the filtrate was concentrated to dryness under reduced pressure. The crude product was purified by chromatography on a column of silica gel 60 (100 g) with (95:5) chloroform/methanol as the eluting solvent. Effluent fractions that were shown by means of a recording UV monitor to contain the desired product were combined and concentrated to dryness. The residue was titurated with (1:1) methanol/ethylacetate (5 ml) and the crystalline product was collected by filtration MS: m/z 259 (M+, $C_{10}H_{14}N_3O_4F$).

(d) 5-Azidomethyl-1-(2,3-dideoxy-3-fluoro-β-D-ribofuranosyl)uracil

A suspension of the bromination product obtained from 2.86 g (10 mMol) 5'-O-acetyl-3'-fluorothymidine, 3.25 g (50 mMol) sodium axide and 100 ml of dry 1.4-dioxane was heated under gentle reflux for 3 hours. After cooling to room temperature the solution was filtered and concentrated under vacuum to a solid residue. Water (50 ml) and chloroform (30 ml) were added to the above residue, and, after removing of the organic layer the water solution was extracted successively with three 30 ml portions of chloroform. The combined chloroform phases were concentrated under reduced pressure to a brown residue. The O-acetyl group was removed by standard procedure with ammonia/methanol. The desired product was isolated by chromatography of the crude product on a column of silica gel 60 (150 g) with (95:5)chloroform/methanol as eluting solvent. Fractions that were shown by thin layer chromatography (TLC) to contain the desired product were combined and concentrated in vacuum to a pale yellow colored solid. MS: m/z 285 (M+, $C_{10}H_{12}N_5O_4F$).

EXAMPLE 5

Preparation of 2',3'-dideoxy-3'-fluoropurineribosides by fluorination of corresponding xylo derivatives with dialkylaminosulfur trifluoride 9-(2,3-Dideoxy-3-fluoro-β-D-ribofuranosyl)-2-fluoroadenine (2',3'-dideoxy-3'-fluoro-2-fluoroadenosine) 10 mMol 9-(5-O-acyl-2-deoxy-β-D-xylofuranosyl-2-fluoro-adenine dissolved in 10 ml chloroform and added to a solution of 11 mMol diethylaminosulfur trifluoride in 30 ml chloroform, which had been cooled to −75° C. The reaction mixture was slowly heated to room temperature and added to 100 ml ice cold water. The organic phase was separated, washed with sodium bicarbonate and water and dried over sodium sulfate. After expelling the chloroform under vacuum a product was obtained, the O-acyl group of which was removed in a known manner. A column chromatographic separation on silica gel with chloroform (5% methanol) as eluent yielded the title compound as a solid substance MS: m/z 271 (M+, $C_{10}H_{11}O_2N_5F_2$).

EXAMPLE 6

Transglycosidation to obtain 2- or 2,6-substituted 2',3'-dideoxy-3'-fluoropurine ribosides 9-(2,3-Dideoxy-3-fluoro-β-D-ribofuranosyl)-2-fluoroadenine A mixture of 2.88 g (10 mMoles) 1-(5-0-acetyl-2,3-dideoxy-3-fluoro-β-D-ribofuranosyl) thymine 4.6 g (30 mMol) 2-fluoroadenine, 7.4 ml bistrimethylsilyl acetamide, and 250 ml acetonitrile was heated on reflux for 25 minutes. Subsequently, 6.5 ml (33 mMol) trifluoromethanesulfonic acid trimethylsilyl ester was added and the reaction mixture heated on reflux for further 8 hours. After removal of the solvent under vacuum the residue was suspended in 100 ml chloroform and neutralized with NaHCO$_3$ solution. The organic phase was dried over sodium sulfate filtered and the chloroform removed under vacuum. The residue was separated by column chromatography on silica gel, eluting with chloroform (1 l of 5% n-hexane; 1.5 l of 2.5% n-hexane; 1 l of 1 % n-hexane). The obtained mixture was deacetylated in a conventional manner by means of ammonia/methanol and was subjected to column chromatographic separation. Chloroform (1% methanol) was used as eluent. 0.515 g was isolated of the $\beta$-anomer, the title compound. Further compound remained in the mixture with the a-anomer.

EXAMPLE 7

Preparation of 5-substituted 2',3'-dideoxy-3'fluorocytidines from the corresponding uridine 1-(2,3-Dideoxy-3-fluoro-$\beta$-D-ribofuranosyl)-5-methylcytidine (2',3'-dideoxy-3'-fluoro-5-methylcytidine
1.5 g (5.2 mMol) 5'-0-acetyl-3'-fluorothymidine was dissolved in 25 ml pyridine and mixed with 760 mg (11 mMol) triazole and 1.96 g (8 mMol) $\beta$-chlorophenoxyphosphoric acid dichloride. The reaction mixture remained at room temperature for 5 days. Subsequently 30 ml dioxane in conc. ammonia (3:1 vol/vol) were added. The solution was concentrated under vacuum, the resulting residue was dissolved in water and charged into a 70 ml column of DOWEX 50 W×8 (H+-form). The column was eluted first with 800 ml water and then with 600 ml 5% ammonia solution. 0.8 g, 2',3'-dideoxy-3'-fluoro-5-methylcytosine was obtained as the hydrochloride from the corresponding fractions, containing UV-absorbine product, after expulsion of the solvent and crystallization from methanol (brought to pH 2 with HCl). Melting point 177° C. (decompoistion), MS: m/z 243 (M+, C$_{10}$H$_{14}$O$_3$N$_3$F).

EXAMPLE 8

Preparation of 3'-deoxy-3'-fluoro-arabinosylcytosine from (3'-deoxy-3'fluoro-$\beta$-D-arabinosyl)urea A mixture of 2.45 g (20 mMol) 3'-deoxy-3'-dluoroarabi-nosyluracil, 1.52 g (12 mMol) triazole, 4.0 g (16 mMol) p-chlorophenoxyphosphoric acid dichloride in 50 ml pyridine was treated as in Example 5.

After separation of the reaction mixture on a column packed with DOWEX 50 W×8 (H+-form), 1.53 g of the title compound were obtained from methanol/HCl at pH 2 as hydrochloride, MS: m/z 246 (M+, C$_9$H$_{11}$O$_5$N$_2$F).

EXAMPLE 9

3'-deoxy-3'-fluoro-5'-O-palmitoyl-thymidine

At 0° C., 1.2 equivalents of palmitoyl chloride were added to a solution of 3'-deoxy-3'-fluorothymidine in pyridine. The solution was warmed slowly to room temperature. As soon as a thin layer chromatographic control (CHCl$_3$/methanol=95/5 on silica gel) showed a complete reaction, the solution was poured into ice water. The aqueous phase was decanted, the resulting oil was chromatographed on silica gel with chloroform eluent. The title compound was recovered from the suitable fractions by evaporation of the solvent. M.P. 65°-66° C. (cyclohexane).

EXAMPLE 10

Preparation of 5'-0-acetyl-3'-deoxy-3'-fluorothymidine 56 mMol acetanhydride was added at 0° C. to a solution of 50 mMol 3'-deoxy-3'-fluorothymidine in 50 ml pyridine. The reaction solution stands overnight at room temperature and was subsequently poured into ice water. The aqueous phase was decanted. The oily product was purified on silica gel with chloroform eluent, the corresponding fractions gave a solid material which was recrystallized from ethanol. M.P.97°-98° C.

The esters of other 3'-fluorinated nucleosides were produced similarly as in Examples 9 or 10 from the corresponding acid chloride or anhydride.

EXAMPLE 11

Preparation of the 5'-monophosphate of 3'-deoxy-3'-fluorothymidine 1 mMol 3'-deoxy-3'-fluorothymidine was dissolved in 3 ml trimethylphosphate and the solution was cooled to −3° C. 3 mMol phosphor oxychloride was added to this solution while stirring. The reaction solution was rested at −3° C. for 24 hours. Then 5 ml water was added and the solution was neutralized with triethylamine. The reaction mixture was purified on a 2×35 mm column with dEA-Sephadex A-25 packing and eluted with pH 7–8 triethylammonium hydrogen carbonate with a linear gradient of 0–0.4 M. The monophosphate was obtained as the triethylammonium salt from the corresponding fractions after removing the buffer solution.

EXAMPLE 12

Preparation of the sodium salt of the 5'-monophosphate of 3'-deoxy-3'-fluorothymidine The nucleotide obtained in Example 11 was dissolved in a small volume of methanol and is reacted dropwise with 0.5 ml of a molar solution of sodium iodide in acetone. The resulting precipitate was centrifuged several times, each washed with 5 ml dry acetone and dried in vacuum over phosphorus pentoxide.

EXAMPLE 13

Hydrogen form of 3'-deoxy-3'-flourothymidine-5'-monophosphate

The hydrogen form of the monophosphate was prepared by dissolving the ammonium salt obtained in Example 11 in 4 ml water and passing it through a column packed with 3 ml DOWEX-50 W×8 (H+-form) ion exchange resin.

EXAMPLE 14

0.1 mMol of the monophosphate prepared in accordance with Example 11 was changed into the corresponding pyridinium salt by passing it through DOWEX-50 W×8 cation exchange resin (pyridinium form). By adding 2 equivalents tri-n-butylamine, the tributylammonium salt was obtained which was then further treated through repeated adding of dry pyridine and N,N-dimethylformamide and evaporation of the solvent. 0.5 mMol 1,1'-carbonylbis(imidazole) is added to the solution of the anhydrous tributylammonium salt in 2 ml dimethylformamide. The progress of the reaction was controlled by thin layer chromatography (cellulose: 6/3/1=isopropanol/conc. ammonia/water). After completion of the reaction 35 μl methanol was added and the reaction solution was rested for 15 minutes at room temperature. Next 0.5 mMol tributylammonium pyrophosphate (prepared from the pyridinium salt by adding 4 equivalents tributylamine) in 5 ml N,N-dimethlyformamide was added, and the mixture was rested for several hours at room temperature. After removing of the solvent the triphosphate was purified on a 2×35 cm DEAE-Sephadex A-25 column with a linear gradient of 0.05–0.6M triethylammonium hydrogen carbonate buffer.

EXAMPLE 15

Preparation of the 5'-diphosphate of 3'-deoxy-3'-flourothymidine 0.3 mMol of the hydrogen-form of the monophosphate obtained in Example 13, was dissolved in 5 ml water. 1.2 mMol morpholine was added and the solution was heated under reflux. During a 3 hour period a solution of 1.2 mMol dicyclohexylcarbodiimide in 4 ml tert-butanol was added. The reaction solution was held under reflux for 12 hours, cooled, filtered and the solvent was removed. Ethanol was added and the solvent is again driven off. The procedure was repeated three times. The residue was dissolved in a small amount of methanol and the phosphormorpholidate precipitates by addition of ether. By reacting the precipitate four times, each time with 10 ml pyridine, and removal of the solvent, the phosphomorpholidate is dried and finally dissolved in 5 ml pyridine. This solution is reacted with 2 mMol bis(tri-N-butyl- ammonium)-pyrophosphate and is held overnight at room temperature. Finally the solvent is removed. The residue was dissolved in 70 ml water and charged on a 2×25 cm DEAE-Sephadex A-25 column, which was equilibrated with 0.05 mMol ammoniumbicarbonate. The phosphates were eluted with a linear gradient of 0.05–0.8 Mol of ammoniumbicarbonate. The corresponding fractions which contain the diphosphate nucleoside, were combined, as well as those which contain the triphosphate nucleoside. Each of the combined fractions were dried under vacuum, dissolved again in water, dried again, then dissolved in water and freeze-dried.

EXAMPLE 16

9-(2,3-Dideoxy-3-fluoro-β-ribofuranosyl)-6-thioguanosine

A mixture of 2.88 g (10 mMol) 1-(5-0-acetyl-2,3-dideoxy-3-fluoro-β-D-ribofuranosyl) thymine, 5.04 g (30 mMol) 6-thioguanine, 7.4 ml bistrimethylsilyl acetamide and 250 ml acetonitrile was heated at reflux for 40 minutes with stirring. Subsequently 6.5 ml (33 mMol) of trifluoromethanesulfonic acid trimethylsilylester was added and the reaction mixture is refluxed for 8 hours. The solvents were evaporated, th syrupy residue was suspended in 100 ml of chloroform and neutralized with NaHCO$_3$ solution. The chloroform extract was filtered, dried with sodium sulfate and concentrated to a small volume. The residue was chromatographed over a column of silica gel G 40 (35×2.5 cm). The column was washed successively with 500 ml each of 5% n-hexane-CHCl$_3$, 2.5% n-hexane-CHCl$_3$, 1% n-hexane-CHCl$_3$, and CHCl$_3$. The corresponding fractions containing the desired purine nucleoside as a mixture of the anomers, were combined and evaporated to dryness. The obtained protected nucleoside mixture was dissolved while stirring in a freshly prepared solution (about 50 ml/4 m equivalents of nucleoside) of 0.3N sodium methoxide. When thin layer chromatography indicated that the reaction was complete, an equivalent of water was added and the solution was neutralized by the addition of DOWEX 50 W×8 (pyridinium-form) ion-exchange resin. The resin was filtered and the filtrate was evaporated to dryness. The residue was applied to a column of silica gel G 40 (35×2.5 cm) which was eluted with chloroform (1% methanol). Evaporation of the appropriate fractions led to the isolation of the title compound (0.47 g). MS: m/z 285 (M+,C$_{10}$H$_{12}$N$_5$O$_2$SF).

EXAMPLE 17

2,6-Diamino-9-(2,3-dideoxy-3-fluoro-β-D-ribofuranosyl) purine

A mixture of 2.88 g (10 mMol) 1-(5-0-acetyl-2,3-dideoxy-3-fluoro-β-D-ribofuranosyl) dhymine. 7.16 g (20 mMol) 2,6-bis-(aminobenzoyl) prine and 5 ml bis-trimethylsilyl acetamide in 200 ml acetonitrile was heated at reflux for 35 minutes with stirring. Trifluoromethanesulfonic acid trimethylsilylester 6.5 ml (33 mMol) was added and the reaction mixture was refluxed for 10 hours. After the mixture was cooled, the solvent was removed, and the residue was dissolved in chloroform, neutralized with NaHCO$_3$ and filtered of insoluble materials. The filtrate is evaporated and the residue is chromatographed over a column of silica gel G 40 (35×2.5 cm) using CHCl$_3$ (1% n-hexane) as the eluent. The obtained protected nucleosides were a mixture of anomers. The protecting groups were removed by treatment with a solution of 0.3N sodium methoxide. The solution was neutralized by the addition of DOWEX 50 W×8 (pyridinium-form)ion-exchange resin. The resin was filtered and the filtrate was evaporated to dryness. The residue was applied to a column of silica gel G 40 (35×2.5 cm) which was eluted with chloroform. The corresponding fractions were evaporated to give 0.23 g 2,6-diamino-9-(2,3-dideoxy-3-fluoro-β-D-ribofuranosyl) purine. MS: m/z 268 (M+, C$_{10}$H$_{13}$N$_6$O$_2$F).

EXAMPLE 18

2-Amino-9-(2,3-dideoxy-3-fluoro-β-D-ribofuranosyl) purine

A solution 2.88 g (10 mMol) 1-(5-0-acetyl-2,3-dideoxy-3-fluoro-β-D-ribofuranosyl) thymine. 7.17 g (30 mMol) 2-aminobenzoyl purine and 7.4 ml bistrimethylsilyl acetamide in 250 ml acetonitrile was heated at reflux for 30 minutes with stirring. Subsequently 6.5 ml (33 mMol) trifluormethanesulfonic acid trimethylsilylester was added and heating was continued for 7 hours. The solvent was removed under reduced pressure, the residue was dissolved in 100 ml chloroform and neutralized with a saturated solution NaHCO$_2$. The organic layer was separated and the solvent was evaporated under vacuum. The residue was chromatographed on a column of silica gel G 40 (35×2.5 cm), using chloroform (1% n-hexane) as the eluent. The obtained mixture of the protected anomers of the purine nucleoside was dissolved in a freshly prepared solution of 0.3 N sodium methoxide. When thin layer chromatography indicated that the reaction was complete in about 2–3 hours, water (10 ml) was added, and the solution was neutralized to pH6–7 by the addition of DOWEX 50 W×8 (pyridinium-form) ion-exchange resin. The resin was filtered and washed with methanol and water, and the combined filtrates were evaporated to dryness. The residue was dissolved in water and repeatedly washed CHCl₃ and Et₂O. The aqueous phase was then filtered and evaporated to dryness. Chromatography of the residue on a silica gel column using chloroform (1% methanol) as eluent led, after evaporation of the appropriate fractions, to the isolation of 0.15 g of 2-amino-9-(2,3-dideoxy-3-fluoro-β-D-ribofuranosyl) purine. A substantial amount of the title compound remained in the mixture with the α-anomer. MS: m/z 253 (M+, $C_{10}H_{12}N_5O_2F$).

We claim:

1. A method for treating AIDS, which comprises administering to a patient in need therefor a pharmaceutical composition comprising a therapeutically effective amount of a compound having the formula

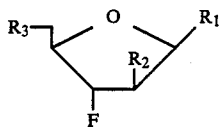

(I)

wherein:
$R_1$ is an adenine, cytosine, guanine, thymine, uracil, 5-substituted uracil, 5-substituted cytosine derivative, 2-fluoroadenine, 2,6-diaminopurine, 2-aminopurine, 6-thioguanine, or 7-deazadenine group;
$R_2$ is H, or a OH group;
$R_3$ is a OH, O-acyl, O-palmitoyl group, or phosphates (as free acid, or its alkali, ammonium or alkyl ammonium salts), or any other precursor group for the hydroxyl group;
or a physiologically acceptable salt thereof.

2. The method of claim 1, wherein said compound is one or more of
2',3'-dideoxy-3'-fluorothymidine,
2'-3'-dideoxy-3'-fluoro-5-bromouridine,
2',3'-dideoxy-3'-fluoro-5-ethyluridine,
2',3'-dideoxy-3'-fluoro-2-fluoroadenosine,
2',3'-dideoxy-3'-fluoro-6-thioguanosine,
2',3'-dideoxy-3'-fluoro-2-aminopurineriboside,
3'-deoxy-3'-fluoroarabinosylthymine,
2',3'-dideoxy-3'-fluoro-5-fluorocyidine,
2',3'-dideoxy-3'-fluoro-5-formylcytidine,
2',3'-dideoxy-3'-fluoro-5-aminouridine,
2',3'-dideoxy-3'-fluoro-5-azidouridine,
2',3'-dideoxy-3'-fluorouridine,
2',3'-dideoxy-3'-fluoro-2,6-diaminopurineriboside,
2',2'-dideoxy-3'-fluoro-5-aminomethyluridine,
2',3'-dideoxy-3'-fluoro-5-azidomethyluridine,
2',3'-dideoxy-3'-fluoro-5-hydroxymethyluridine,
2',3'-dideoxy-3'-fluoocytidine,
3'-deoxy-3'-fluoroarabinosylcytosine,
3'-deoxy-3'-fluoroarabinosyladenine, and
2',3'-dideoxy-3'-fluoro-5-chlorouridine.

3. The method of claim 1, wherein the composition further comprises a pharmaceutically acceptable carrier.

4. The method of claim 4, wherein the composition further comprises a flavoring agent.

5. The method of claim 1, wherein the composition is in a dosage form suitable for administration by injection, infusion, oral ingestion, or anal application.

6. The method of claim 1, wherein the composition is in a dosage form of a coated or uncoated tablet, a capsule, powder, granule, suppository, in the form of a unit dose or a multiple thereof.

7. A method for treating AIDS, which comprises administering to a patient in need therefor a pharmaceutical composition comprising a therapeutically effective amount of a compound having the formula

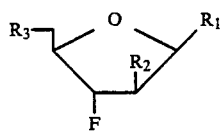

(I)

wherein:
$R_1$ is an adenine, cytosine, quanine, thymine, uracil, 5-substituted uracil, 5-substituted cytosine derivative, 2-fluoroadenine, 2,6-diaminopurine, 2-aminopurine, 6-thioguanine, or 7-deazaadenine group;
$R_2$ is H, or a OH group;
$R_3$ is a OH, O-acyl, O-palmitoyl group, or phosphates (as free acid, or its alkali, ammonium or alkyl ammonium salts), or any other precursor group for the hydroxyl group;
or a physiologically acceptable salt thereof, provided that when $R_2$ is H, and $R_3$ is OH, then $R_1$ is not thymine, cytosine, adenine, or guanine.

8. The compounds:
2',3'-dideoxy-3'-fluoro-2-fluoroadenosine,
2',3'-dideoxy-3'-fluoro-6-thioguanosine,
2',3'-dideoxy-3'-fluoro-2,6-diaminopurineriboside, and
2',3'-dideoxy-3'-fluoro-2-aminopurineriboside.

* * * * *